United States Patent [19]

Jacobs, III et al.

[11] Patent Number: 5,180,835

[45] Date of Patent: Jan. 19, 1993

[54] PROCESS FOR THE PREPARATION OF MONOMERIC TETRAMETHOXYMETHYLGLYCOLORIL

[75] Inventors: William Jacobs, III, Bethel; Fred W. Luciw, Stamford, both of Conn.; Ilze B. Kancans, Hartsdale, N.Y.; Daniel W. Thomas, Bridgewater, N.J.; Leslie Boldizer; Robert G. Lees, both of Stamford, Conn.

[73] Assignee: American Cyanamid Company, Stamford, Conn.

[21] Appl. No.: 720,302

[22] Filed: Jun. 25, 1991

[51] Int. Cl.$^5$ .......................................... C07D 487/04
[52] U.S. Cl. .................................................. 548/303.4
[58] Field of Search .......................................... 548/304

[56] References Cited

U.S. PATENT DOCUMENTS

| | | | |
|---|---|---|---|
| 3,927,024 | 12/1975 | Savostianoff | 260/309.7 |
| 4,064,191 | 12/1977 | Parekh | 260/850 |
| 4,101,520 | 7/1978 | Boldizar | 528/248 |
| 4,105,708 | 8/1978 | Parekh | 260/849 |
| 4,118,437 | 10/1978 | Parekh | 260/834 |
| 4,137,213 | 10/1979 | Kempter | 260/39 P |
| 4,254,235 | 3/1981 | Turpin | 525/162 |
| 4,255,558 | 3/1981 | Turpin | 528/245 |
| 4,293,692 | 10/1981 | Pai | 544/196 |
| 4,346,144 | 8/1982 | Craven | 428/335 |
| 4,520,167 | 5/1985 | Blank | 525/131 |
| 4,683,271 | 7/1987 | Lin et al. | 525/403 |
| 4,877,838 | 10/1989 | Toman | 525/107 |

FOREIGN PATENT DOCUMENTS

| | | |
|---|---|---|
| 920146 | 10/1954 | Fed. Rep. of Germany . |
| 848400 | 9/1960 | United Kingdom . |
| 2010875 | 7/1979 | United Kingdom . |
| 1562971 | 3/1980 | United Kingdom . |

OTHER PUBLICATIONS

Houben-Weyl, "MacRomolekulare Stoffe", vol. XIV, Part 2, p. 353 (1960).
Jour. of Coatings Tech., vol. 51, No. 658 pp. 101-110, 1979 "Chemistry of Glycolurilresins & Performance".
Proceedings of 16th Inter. Conf. in Organic Coating Science & Tech., vol. 16, pp. 509-524, Jul. 9-13, 1990.
Textile Research Jour., vol. 41, pp. 239-254, 1971 "Advance in Chemistry of N-Containing Crosslinking".

Primary Examiner—Joseph Paul Brust
Assistant Examiner—Mary Susan H. Gabilan
Attorney, Agent, or Firm—Frank M. Van Riet

[57] ABSTRACT

Described is an improved process for the preparation of fully methylolated, substantially fully etherified, and substantially monomeric tetramethoxymethlglycoluril useful as a crosslinking agent for powder coatings. The improved process adds after the conventional steps of methylolation and etherification the new steps of acidic distillation followed by an additional etherification.

13 Claims, 2 Drawing Sheets

PROCESS FOR THE PREPARATION OF MONOMERIC TETRAMETHOXYMETHYLGLYCOLORIL

FIELD OF THE INVENTION

This invention relates to an improved process for the preparation of a substantially fully methylolated, substantially fully etherified, substantially monomeric tetramethoxymethylglycoluril crosslinking agent.

BACKGROUND OF THE INVENTION

Tetramethoxymethylglycoluril crosslinking agents are known. They are prepared by etherification of tetramethylolglycoluril with excess methanol under acidic conditions. The unreacted methanol is then removed under basic conditions to prevent acid catalyzed oligomerization of tetramethoxymethylglycoluril.

Tetramethoxymethylglycoluril chemistry is described in the following references: U.S. Pat. Nos. 4,118,437; 4,064,191; 4,877,838; 4,105,708; 4,520,167; 3,927,024 and 4,137,213; British Patent Number 1,562,971 and 2,010,875; German Patent Number 920,146 (Chemical Abstracts, Volume 52 (1958), page 11, 469 d, e, and f) and Houben-Weyl Makromolekulare Stoffe, Volume XIV, Part 2, page 353. In the prior art processes for the preparation of tetramethoxymethylglycoluril above, the unreacted methanol is removed by distillation under basic conditions.

Several aspects of tetramethoxymethylglycoluril chemistry are described in an article entitled "Chemistry of glycoluril-formaldehyde resins and their performance in coatings," Journal of Coatings Technology, Volume 51, Number 658, pages 101 to 110, 1979. Further aspects of glycoluril chemistry are described in the following articles entitled "Advances in the chemistry of N-containing crosslinking agent," Textile Research Journal, Volume 41, pages 239 to 254, 1971, and "New Crosslinking Agents for Durable Powder Coatings," Proceedings of the 16th International Conference in Organic Coating Science and Technology, Athens, Greece, Volume 16, pages 509 to 524, Jul. 9 to 13, 1990.

U.S. Pat. Nos. 4,101,520 and 4,293,692 describe methylolated and etherified melamines.

Powder coatings prepared from teramethoxymethylglycoluril are described in U.S. Pat. Nos. 4,118,437; 4,254,235; 4,255,558; 4,683,271; 4,877,838; and 4,346,144.

Acid catalyzed oligomerization of etherified glycolurils during the removal of alcohols after neutralization with caustic soda or under acidic conditions is described in the British Patent Number 848,400.

The preparative methods of the prior art comprise methylolating glycoluril with formaldehyde, etherifying the resulting tetramethylolglyco uril with excess methanol under acidic conditions, and isolating the reaction product, typically by separating the unreacted methanol by distillation under basic conditions. The distillation is carried out under basic conditions to prevent any potential acid catalyzed oligomerization of tetramethoxymethylglycoluril. However, under the basic conditions of the prior art, an undesirable demethylolation side reaction takes place and, as a result of the demethylolation, products having few methoxymethyl groups are obtained.

Obtaining methoxymethylated glycolurils of high functionality such as those having four methoxymethyl groups per each glycoluril moiety is highly desirable because systems having fewer than four methoxymethyl groups exhibit a diminished efficiency to act as crosslinking agents. In cases where the tetramethoxymethylglycoluril prepared by the methods of the prior art is highly functionalized with methoxymethyl groups, it also contains high levels of oligomers. In cases where the tetramethoxymethylglycoluril contains low levels of oligomers, it also is of low methoxymethyl functionalization. Thus, the tetramethoxymethylglycolurils prepared by the methods of the prior art have either low levels of oligomers accompanied by substantially less than four methoxymethyl groups per glycoluril moiety, or high levels of oligomers accompanied by low levels of the highly functionalized tetramethoxymethylglycoluril. It is therefore desirable to be able to prepare highly functionalized and highly monomeric tetramethoxymethylglycoluril.

It is the object of this invention to provide a process for preparing a substantially fully methylolated, substantially fully etherified, substantially monomeric tetramethoxymethylglycoluril.

SUMMARY OF THE INVENTION

This invention is an improved process for the preparation of tetramethyoxymethylglycoluril which is useful as crosslinking agent and particularly useful as crosslinking agent for powder coatings formulations. The improved process of the invention comprises the addition of two critical steps to the conventional process for forming tetramethoxymethylglycoluril. These additional improvement steps added after conventional methylolation and etherification are distillative separation of volatiles at a pH of from about 5.0 to less than 7, and further etherification to produce substantially fully methylolated, substantially fully etherified, substantially monomeric tetramethoxymethylglycoluril.

This invention is also a product prepared by the improved method of the invention.

DETAILED DESCRIPTION OF THE INVENTION

Figure 1:
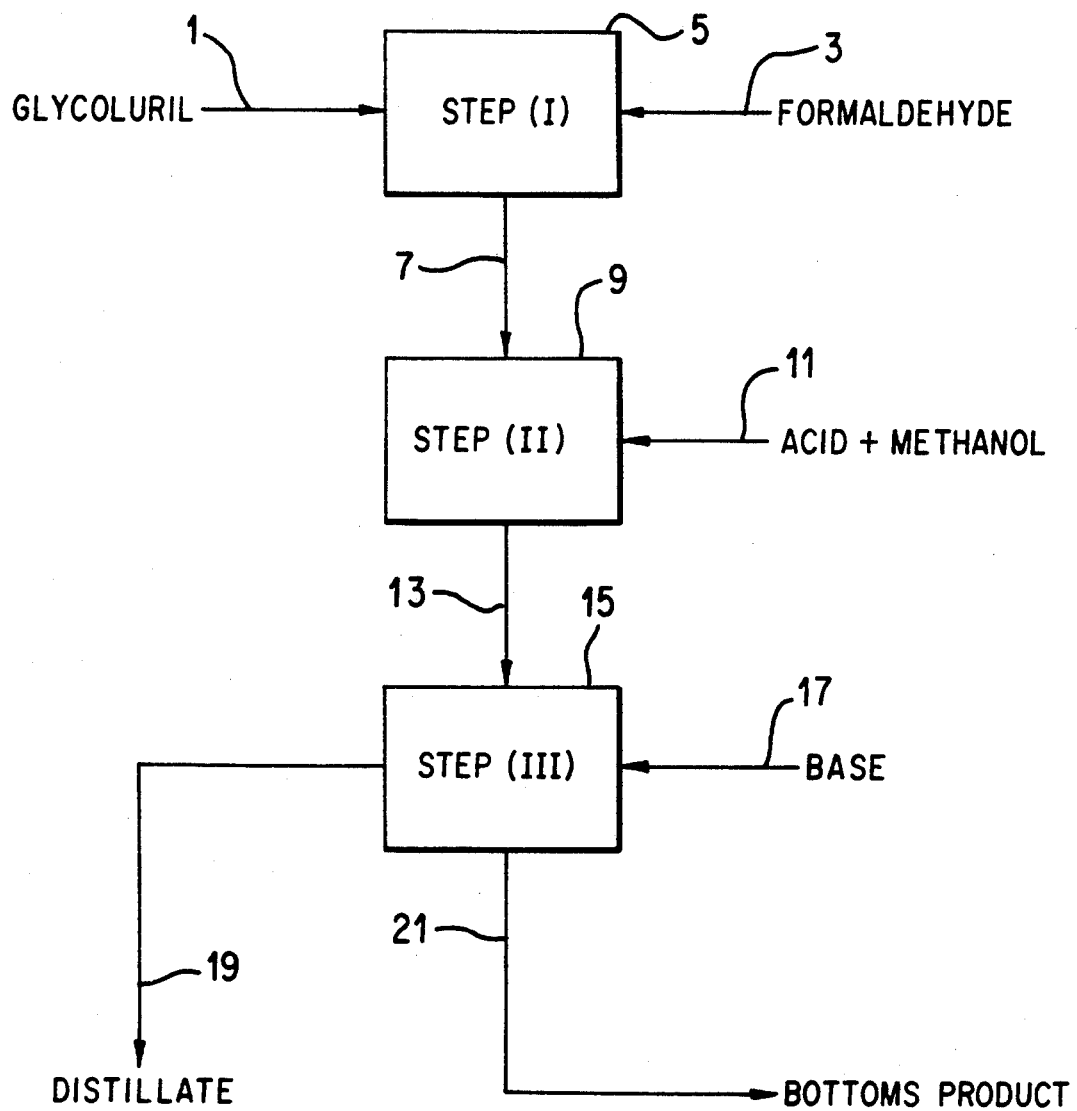
FIG. 1 schematically illustrates a conventional prior art methylolation and etherification process for the production of tetramethoxymethylglycoluril.

In the prior art, tetramethoxymethylglycoluril has been prepared by a process having the essential sequential steps of: (I) methylolating glycoluril with formaldehyde to produce tetramethylolglycoluril, (II) etherifying the tetramethylolglycoluril with excess methanol in a volatile solvent to give tetramethoxymethylglycoluril, and (III) isolating the etherification product.

THE ADVANTAGES OF THE PROCESS OF THE INVENTION

The examples of prior art, have only a single etherification step, with the step of separating by distillation always carried out under basic conditions.

In the examples of the prior art, the etherification step leads to a partially methylolated and partially etherified product even though the precursor is fully methylolated. Because unetherified methylol groups demethylolate under the basic distillation conditions of the isolation step (III), the methods of the prior art produce an incompletely methylolated, and an incompletely etherified product.

The improved process of the invention overcomes the problems of incomplete etherification and demethylolation by adding between steps (II) and (III) of the prior art process the steps of:

(IIa) separating the volatiles from the partially etherified glycolurils by distilling at mildly acidic conditions to prevent demethylolation, and then (IIb) etherifying further to effect substantially complete etherification.

The steps (I), (II), and (III) of the conventional process together with the improvements embodied in the additional steps (IIa) and (IIb) are more fully described below:

In the improved process of the invention, the improvement comprises adding the sequential steps of:

(IIa) separating the volatiles by distilling at a pH in the range of from about 5.0 to about less than 7, a temperature, pressure, and length of time sufficient to produce substantially fully methylolated, partially etherified, substantially monomeric tetramethoxymethylglycoluril, and (IIb) etherifying further the partially etherified tetramethoxymethyl glycoluril with added methanol under acidic conditions to produce a substantially fully methylolated, substantially fully etherifield, substantially monomeric tetramethoxymethylglycoluril having a monomeric tetramethoxymethylglycoluril content in the range of from about 80 weight percent to 100 weight percent, a methoxy to methylene group ratio in the range from about 0.95 to about 1.00, and a methylene to glycoluril ratio in the range of from about 3.7 to about 4.00.

The terms "partial etherification" and "partially etherified" herein mean that within the range of from about 60 percent to less than 95 percent of the methylol groups in the methylolated glycoluril have been transformed to the corresponding methoxymethyl groups.

The term "substantially fully etherified" herein means that from 95 percent to 100 percent of the methylol groups in the methylolated glycoluril have been transformed to the corresponding methoxymethyl groups.

The term "substantially fully methylolated" herein means that from about 95 percent to 100 percent of the N-H groups in glycoluril have been converted to N-methylol groups.

The term "substantially monomeric" tetramethoxymethylglycoluril product herein means that about 80 weight percent to 100 weight percent of the product consists of the monomeric tetramethyloxymethylglycoluril represented by the formula:

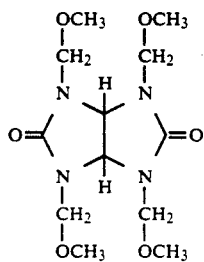

The term "degree of etherification" herein has a meaning identical with "percent etherification." A tetramethylolglycoluril having a degree of etherification of 100 percent is 100 percent etherified.

The term "methoxy to methylene ratio" herein is the ratio of $CH_3$ to $CH_2$ groups, and in the case of tetramethoxymethylglycoluril represented by the formula above the ratio is 1.

The term "methylene to glycoluril ratio" is the ratio of the number of $CH_2$ group to each glycoluril moiety, and in the case of tetramethoxymethylglycoluril represented by the formula above the ratio is 4.00.

Step (I) of the process is carried out by methylolating glycoluril with aqueous and/or methanolic formaldehyde. The mole ratio of formaldehyde to glycoluril is at least 4:1, and preferably the mole ratio of the formaldehyde to glycoluril is from 4.5:1 to 6:1. The methylolation step could be carried out under acidic or under basic conditions, and at near room temperature or higher temperatures.

Step (II) of the process is the conventional etherification step and is carried out under acidic conditions, typically at a pH in the vicinity of one or two. The etherification is done in the presence of excess methanol.

In the practice of the process of the invention, aqueous nitric acid and aqueous sodium hydroxide are the preferred reagents for adjusting the pH of the reaction mixtures. Other acids such as sulfuric, hydrochloric, phosphoric, polyphosphoric, alkyl and aryl sulfonic acids may also be used satisfactorily in carrying out the process of the invention. Similarly, bases other than sodium hydroxide may also be used. Examples of bases usable in the process of the invention are bases such as potassium hydroxide, ammonium hydroxide, sodium or potassium carbonate, triethylamine, and the like.

The pH range in step (IIa), the step of separating the volatiles by distilling, is in the range of about 5 to less than 7, and preferably of from 5.0 to 6.9, and most preferably the pH is in the range of from 5.8 to 6.2.

The solvent in the process of the invention is preferably methanol which is also a reactant. Other volatile solvents which are not reactive with formaldehyde may also be present but their presence is not particularly advantageous since they lead to dilution of the methanol reactant. The term "volatile solvent" herein refers to a solvent having a boiling point in the range of 40° C. to 180° C.

The methanol may be substantially anhydrous or it may contain water. Large quantities of water are to be avoided not only because it leads to dilution of the methanol reactant but also it favors hydrolysis of tetramethoxymethylglycoluril. The preferred solvent in the process of the invention is methanol comprising 0.01 weight percent to about 20 weight percent water.

In step (IIa), the step of separating the volatiles by distilling, the temperature, pressure, and time required to produce substantially fully methylolated, partially etherifield tetramethoxymethylglycoluril have the following ranges: 0° C. to about 150° C. temperature, 1.33 pascals to about 101000 pascals pressure, and 4 hours to about 24 hours time. It is preferable that the temperature is in the range of from about 40° C. to about 75° C., the pressure is in the range of 2000 pascals to about 15000 pascals, and the time is in the range of 4 to about 14 hours.

The weight ratio of the methanol to the total glycoluril-derived components in step (IIa), the step of separating by distilling, is in the range of from about 0.5:1 to about 10:1, and preferably the ratio is in the range of from about 1:1 to about 3:1.

Step (IIb), the novel step of further etherifying the partially etherified tetramethoxymethylglycoluril with added methanol, is carried out to a conversion in the range of from 95 to 100 percent under conventional etherification conditions. Typical of the parameters relating to step (IIb) are the following conditions:

| pH | about 1 |
|---|---|
| Temperature | about 50 to 60° C. |
| Time | about 1 to 2 hours |

Step (III) is the final step of isolating the product. The product isolation of this step may be carried out by one or a combination of known techniques such as distillation, precipitation, crystallization, or solvent extraction. Separating volatile components of the reaction mixture by the technique of distillation in Step III gives a bottoms product which is the tetramethoxymethylglycoluril product of the invention. This step is typically operated under basic conditions. The temperature, pressure, and time parameters useful for performing the distillation to produce a Step III bottoms product of substantially fully methylolated, substantially fully etherified tetramethoxymethylglycoluril have the following ranges:

0° C. to about 150° C. temperature, 1.33 pascals to about 101000 pascals pressure, and 4 hours to about 24 hours time. It is preferable that the temperature is in the range of from about 40° C. to about 130° C., the pressure is in the range of 2000 pasals to about 15000 pascals, and the time is in the range of 4 hours to about 14 hours.

The steps (I), (II), (IIa), (IIb) and (III) of the process may be performed as a batch of continuous process using the same or separate vessels or equipment for accomplishing any or all of the steps.

The process of the invention may be better understood by reference to the FIGURES as follows:

PRIOR ART PROCESS (FIG. 1)

Thus, in FIG. 1 illustrating a conventional process, glycoluril is introduced via line (1) and formaldehyde is introduced via line (3) into a reaction zone (5) where the glycoluril is methylolated. Methylolation is typically carried out at about pH 8 and is generally effected in less than 4 hours.

The methylolated glycoluril reaction product from zone (5) is sent via line (7) to etherification zone (9) and methanol is introduced via line (11) together with acid to give a pH typically of less than 2.

The etherified glycoluril from reaction zone (9) is thereafter sent via line (13) to distillation zone (15) and base is introduced via line (17) to typically raise the pH to about 8. Distillation zone (15) is operated at elevated temperature and subatmospheric pressure to permit removal of volatiles such as water and unreacted methanol via line (19). A prior art tetramethoxymethylglycoluril product is removed via line (21).

IMPROVED PROCESS OF THE INVENTION (FIG. 2)

In the improved process of the invention tetramethoxymethylglycoluril is prepared by a process having two additional process steps used in combination with the essential sequential steps of the prior art (viz, steps I, II, & III) described in the preceding paragraphs of this section. These two additional process steps occur between steps (II) and (III) of the conventional process, that is, between the conventional etherification and distillation steps. The improved process of the invention is a five step process having the essential sequential steps of: (I) methylolating glycoluril with formaldehyde to produce tetramethylolglycolyuril, (II) etherifying the tetramethylolglycoluril with excess methanol in a volatile solvent, (IIa) separating the volatiles by distillation at a pH typically of from about 5 to 6.9, (IIb) further etherifying the Step (IIa) bottoms product (where "bottoms product" is defined as the residue left behind after removal of volatiles as overhead) of step (IIa), and then (III) separating the volatiles by distillation to isolate the tetramethoxymethylglycoluril as Step (III) bottoms product.

Figure 2:
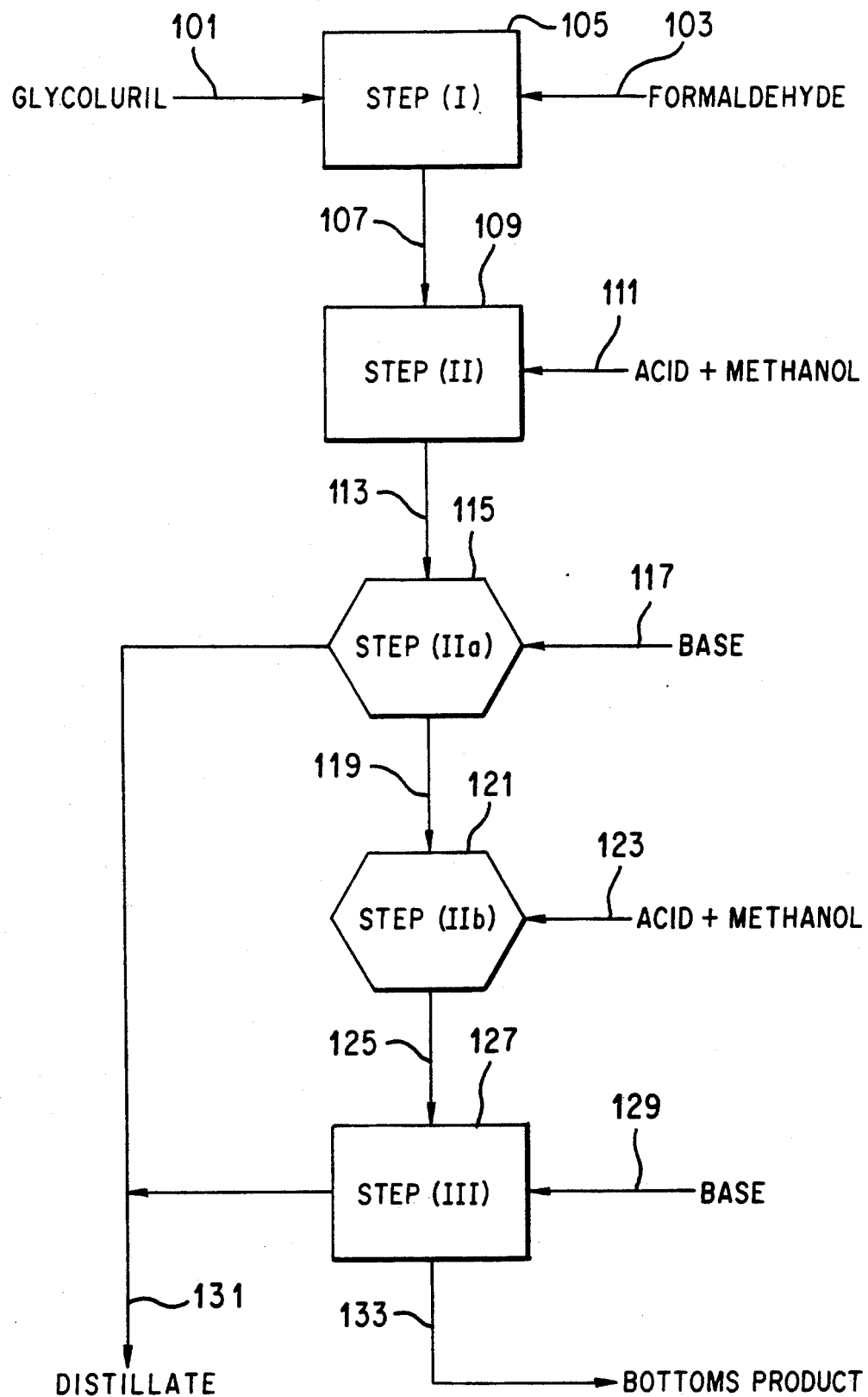
FIG. 2 schematically illustrates the process of the invention and is an improved process for the production of tetramethoxymethylglycoluril.

FIG. 2 illustrates the improved process of the invention using rectangles to symbolize conventional process steps and hexagons to symbolize the added steps (IIa) and (IIb) which constitute the improvement in the process of this invention.

Thus, in FIG. 2, glycoluril introduced via line (101) and formaldehyde introduced via line (103) enter reaction zone (105) where the glycoluril is methylolated. Methylolation is typically carried out at about pH 8 and is generally effected in less than 4 hours.

The methylolated glycoluril reaction product from zone (105) is sent via line (107) to etherification zone (109) and methanol is introduced via line (111) together with acid to give a pH typically of less than 2.

The partially etherified glycoluril from reaction zone (109) is thereafter sent via line (113) to distillation zone (115) and base is introduced via line (117) to adjust the pH typically to a value between about 5 to 6.9. Distillation zone (115) is operated at elevated temperature and subatmospheric pressure to permit removal of volatiles such as unreacted water and methanol via line (131).

The bottoms product of Step (IIa) from distillation zone (115) is sent via line (119) to the second etherification zone (121) and methanol introduced via line (123) together with acid to give a pH typically of less than 2.

The substantially fully etherified glycoluril from etherification reaction zone (121) is thereafter sent via line (125) to distillation zone (127) and base is introduced via line (129) to typically raise the pH to about 8. Distillation zone (127) is operated at elevated temperature to permit removal of volatiles such as unreacted water and methanol via line (131). An improved tetramethoxymethylglycoluril product of the invention is removed via line (133).

The following examples illustrate the invention by comparing a process which is within the scope of the invention (Examples 1 and 2) with a process which is outside the scope of the invention (Example 3).

EXAMPLE 1

1. Part 1

Partially Etherified Tetramethoxymethylglycoluril

A substantially fully methylolated, partially etherified, substantially monomeric tetramethoxymethylglycoluril solution was prepared as follows:

Glycoluril (142.0 g) was methylolated with formaldehyde (179.85 g) in methanol (114.45 g) and water (32.7 g) under basic conditions. After adding additional methanol (270.0 g), the tetramethylolglycoluril was etherified under acidic conditions with 70 weight percent nitric acid at a pH of less than 1 for 1 to 2 hours. The pH was then adjusted to about 6 with a 25 weight percent aqueous sodium hydroxide solution.

2. Part 2

Separation of Volatiles by Distillation: Step (IIa)

The volatiles from the partially etherifield solution at pH 6 prepared by the method described in Part 1 of this example above were removed according to the improved process of the invention, by distilling the volatiles at an initial temperature of 40° C. to a final temperature of about 70° C. and a final pressure of 10000 pascals. The reaction mixture was held at about 70° C. for an additional 30 minutes. During this period (about 10.5 hours), about 250 g of volatiles distilled and were collected. The residue contained partially etherified tetramethoxymethylglycoluril.

3. Part 3

Further Etherification: Step (IIb)

A large excess of anhydrous methanol was added to the residue prepared by the method described in PART 2 of this example above. After cooling to about 55° C. the solution was acidified with 70 weight percent nitric acid to a pH less than 1. After about 1.5 hours, etherification was complete.

4. Part 4

Isolation of the Tetramethoxymethylglycoluril

The reaction product of PART 3 was basified to a PH of 7 to 8 with 20% by wt. sodium hydroxide (per workup procedure of U.S. Pat. No. 4,118,437 and the volatiles were separated to give substantially fully methylolated, substantially fully etherified, substantially monomeric tetramethoxymethylglycoluril, an example of the crosslinker of the invention, having the following properties, as analyzed by high pressure size exclusion chromatography and high pressure liquid chromatography:

| | |
|---|---|
| Crystallization temperature (°C.) | 106–109 |
| Tetramethoxymethylglycoluril monomer (%) | 87.4 |
| Trimethoxymethylglycoluril monomers (%) | 5.9 |
| Other monomers (%) | 3.8 |
| Etherfied oligomers (%) | 2.9 |

EXAMPLE 2

The procedure of Example 1 was repeated up to the isolation stage as described in Parts 1, 2, and 3 of Example 1.

After the further etherification stage of PART 3, Step (IIb), but prior to the final basic distillation stage of PART 4, the reaction mixture was analyzed by High Pressure Size Exclusion Chromatography, High Pressure Liquid chromotography, and 400 MHz Nuclear Magnetic Resonance Spectroscopy.

The product, after further etherification but prior to the final basic distillation, had the following properties:

| | |
|---|---|
| Tetramethoxymethylglycoluril monomer (%) | 87.3 |
| Trimethoxymethylglycoluril monomers (%) | 5.9 |
| Other monomers (%) | 3.9 |
| Etherified oligomer (%) | 3.0 |
| Methoxy to methylene ratio | 0.98 |
| Methylene to glycoluril ratio | 4.0 |
| Tetramethoxymethylglycoluril monomer (mole percent) | 85.0 |

The product obtained by Example 2 has a tetramethoxymethylglycoluril monomer level higher than 80 percent, therefore it is within the scope of the invention.

EXAMPLE 3

Comparative

The procedure of Example 2 was repeated with the exception that step (IIa), isolation by separation of volatiles by distilling step (see PART 2 of Example 1), was carried out at a pH of 7 to 8, (as disclosed by U.S. Pat. No. 4,118,437). The product, after further etherification but prior to the final basic distillation, had the following properties:

| | |
|---|---|
| Tetramethoxymethylglycoluril monomer (%) | 70.4 |
| Trimethoxymethylglycoluril monomers (%) | 19.5 |
| Other monomers (%) | present |
| Etherified oligomer (%) | 10 |
| Methoxy to methylene ratio | 0.99 |
| Methylene to glycoluril ratio | 3.9 |
| Tetramethoxymethylglycoluril monomer (mole percent) | 69.0 |

The product prepared by the method of Example 3 had monomeric tetramethoxymethylglycoluril less than 80 percent, therefore the product of Example 3 is outside of the scope of this invention.

Although the present invention has been described with references to certain preferred embodiments, it is apparent that modifications and changes thereof may be made by those skilled in the art without departing from the scope of this invention as defined by the appended claims.

We claim:

1. In a process for the preparation of tetramethoxymethylglycoluril of the type having the sequential steps of (I) methylolating glycoluril with formaldehyde, (II) etherifying with methanol in a volatile solvent, and (III) isolating the tetramethoxymethylglycoluril product, the improvement comprising adding between steps (II) and (III) the sequential steps of:

(IIa) separating the volatiles by distilling at a pH in the range of from about 5.0 to less than 7, at a temperature, pressure, and for a length of time sufficient to produce substantially fully methylolated, partially etherified, substantially monomeric tetramethoxymethylglycoluril, and (IIb) etherifying further the partially etherified tetramethoxymethylgycouril of step (IIa) with added methanol under acidic conditions to produce a substantially fully methylolated, substantially fully etherified, substantially monomeric tetramethoxymethylglycouril having a monomeric tetramethoxymethylglycoluril content in the range of from about 80 weight percent to 100 weight percent, a methoxy to methylene ratio in the range from about 0.95 to about 1.00, and a methylene to glycoluril ratio in the range of from about 3.7 to about 4.00.

2. The process of claim 1 wherein the pH of step (IIa) is in the range of from about 5.8 to about 6.2.

3. The process of claim 1 wherein the temperatures in step (IIa) is in the range of from about 40° C. to about 75° C.

4. The process of claim 1 wherein the pressure in step (IIa) is in the range of from about 2000 pascals to about 15000 pascals.

5. The process of claim 1 wherein the time in step (IIa) is in the range of from about 4 hours to about 14 hours.

6. The process of claim 1 wherein methanol is used as a solvent in steps (IIa) and (IIb) of the process.

7. The process of claim 1 wherein the methanol in steps (IIa) and (IIb) of the process comprises from about 0.01 to about 20 weight percent water.

8. The process of claim 1 wherein the initial weight ratio of methanol to glycoluril derived components in the reaction zone of steps (IIa) and (IIb) is in the range of from about 0.5:1 to about 10:1.

9. The process of claim 8 wherein the ratio of methanol to glycoluril derived components is in the range of from about 1:1 to about 3:1.

10. The process of claim 1 wherein the initial degree of etherification in the partially etherified tetramethoxymethylglycoluril in step (IIa) is in the range of from about 60 percent to less than 95 percent.

11. The process of claim 1 wherein the final degree of etherification in step (IIb) is in the range of from 95 percent to 100 percent.

12. The process of claim 1 wherein the isolation of product is carried out by a method selected from the group consisting of distillation, precipitation, crystallization, solvent extraction, and a combination of such techniques.

13. The process of claim 12 wherein the isolation technique is distillation conducted under basic conditions.

* * * * *